US006248104B1

(12) United States Patent
Chopin et al.

(10) Patent No.: US 6,248,104 B1
(45) Date of Patent: Jun. 19, 2001

(54) APPARATUS FOR OSTEOSYNTHESIS COMPRISING A CONNECTOR OF THE SPINAL PIN AND THE ANCHORING ELEMENTS

(76) Inventors: Daniel Chopin, 876, Avenue Adolf Leroy, F-62155 Merlimont; Pierre Roussouly, 34, rue Ferroux, F-69450 Saint Cyr au Mont d'Or; Arsene Grosse, 1, rue Sandre, F-67000 Strasbourg; Gilbert Taglang, 9, rue Paul Verlaine, F-67370 Griesheim-Souffel; Jean Moulin, 13, rue de la Viabert, F-69006 Lyon; Jean Saurat, 5, allee des Rochers, F-49240 Avrille, all of (FR)

( * ) Notice: Subject to any disclaimer, the term of this patent is extended or adjusted under 35 U.S.C. 154(b) by 0 days.

(21) Appl. No.: 09/402,220

(22) PCT Filed: Apr. 1, 1998

(86) PCT No.: PCT/FR98/00662

§ 371 Date: May 8, 2000

§ 102(e) Date: May 8, 2000

(87) PCT Pub. No.: WO98/43551

PCT Pub. Date: Oct. 8, 1998

(30) Foreign Application Priority Data

Apr. 1, 1997 (FR) .................................................. 97 03958

(51) Int. Cl.[7] ............................ A61B 17/70; A61B 17/68
(52) U.S. Cl. ............................................. 606/61; 606/60
(58) Field of Search ................................. 606/60, 61, 69, 606/71, 72

(56) References Cited

U.S. PATENT DOCUMENTS

| 1,950,635 | 3/1934 | Steinmayer . |
| 2,391,693 | 12/1945 | Ettinger . |
| 4,620,533 | 11/1986 | Mears . |

(List continued on next page.)

FOREIGN PATENT DOCUMENTS

| 0535623 | * 9/1993 | (EP) | ........................................ 606/61 |
| 0558883 | * 9/1993 | (EP) | ........................................ 606/61 |
| 2 615 095 | 5/1987 | (FR) . | |
| 2 693 365 | 7/1992 | (FR) . | |
| 2 720 923 | 6/1994 | (FR) . | |
| 2 736 258 | 7/1995 | (FR) . | |

Primary Examiner—Gene Mancene
Assistant Examiner—Michael B. Priddy
(74) Attorney, Agent, or Firm—Woodard, Emhardt, Naughton, Moriarty & McNett

(57) ABSTRACT

This instrumentation comprises at least one vertebral rod (1), bone anchoring elements (2) spaced along the rod, a connector (3) connecting the rod to each anchoring element, and pressure means (4) for clamping together the rod, the anchoring element and the connector; each anchoring element has a bearing surface (7) for the rod which is inclined relative to the longitudinal axis (XX) of the anchoring element; in the connector there is provided a cavity (11) providing at least one bearing point for the rod held trapped between said inclined bearing surface and a wall (12) of the cavity, and the latter is extended by a lateral aperture (18) permitting insertion of the vertebral rod radially in its cavity; this instrumentation is easy to use by the surgeon owing to the convenience of insertion of the rod in the connector, and the direct bearing of the rod against the surface (7) of the anchoring element (2) reduces its transverse overall size.

43 Claims, 4 Drawing Sheets

U.S. PATENT DOCUMENTS

| | | | |
|---|---|---|---|
| 4,648,388 | 3/1987 | Steffee . | |
| 4,653,481 | 3/1987 | Howland et al. . | |
| 4,920,959 | 5/1990 | Witzel et al. . | |
| 5,002,542 | 3/1991 | Frigg . | |
| 5,030,220 | 7/1991 | Howland . | |
| 5,047,029 | 9/1991 | Aebi et al. . | |
| 5,403,315 | 4/1995 | Ashman . | |
| 5,423,818 | 6/1995 | Van Hoeck et al. . | |
| 5,437,670 | 8/1995 | Sherman et al. . | |
| 5,470,333 | 11/1995 | Ray . | |
| 5,498,264 | 3/1996 | Schlapfer et al. . | |
| 5,534,002 * | 7/1996 | Brumfield et al. | 606/61 |
| 5,601,552 * | 2/1997 | Cotrel | 606/61 |
| 5,609,592 * | 3/1997 | Brumfield et al. | 606/61 |
| 5,662,651 * | 9/1997 | Tornier et al. | 606/60 |
| 5,688,274 * | 11/1997 | Errico et al. | 606/61 |
| 5,810,817 | 9/1998 | Roussouly et al. . | |
| 5,814,046 * | 9/1998 | Hopf | 606/61 |
| 5,879,350 * | 3/1999 | Sherman et al. | 606/61 |
| 5,989,250 * | 11/1999 | Wagner et al. | 606/61 |
| 6,077,262 * | 6/2000 | Schlapfer et al. | 606/61 |
| 6,106,526 * | 8/2000 | Harms et al. | 606/61 |

\* cited by examiner

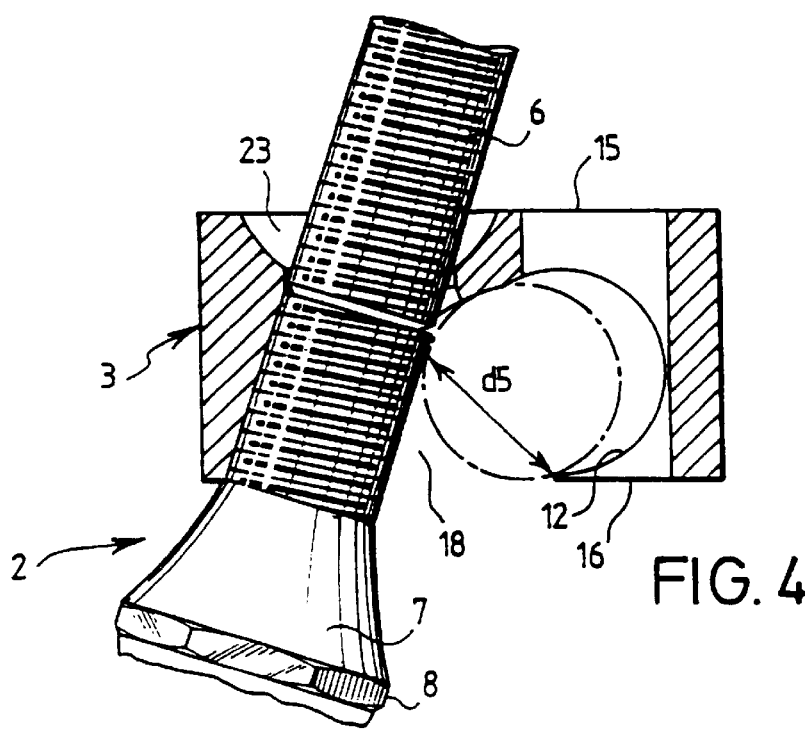
FIG. 4
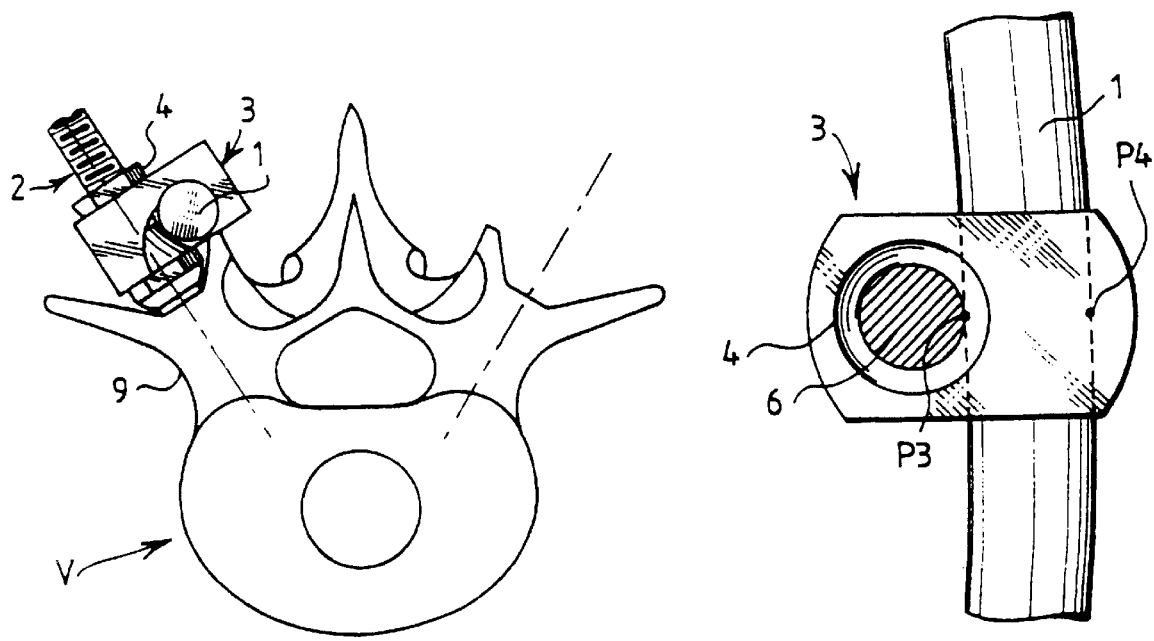
FIG. 5
FIG. 6

APPARATUS FOR OSTEOSYNTHESIS COMPRISING A CONNECTOR OF THE SPINAL PIN AND THE ANCHORING ELEMENTS

The present invention relates to a spinal osteosynthesis instrumentation of the type comprising at least one longitudinal vertebral rod, and preferably two rods, bone anchoring elements having a longitudinal axis and spaced apart along the rod, a connector for connecting the rod to each anchoring element, and pressure means for clamping together the rod, the anchoring elements and the connectors.

Spinal instrumentations of this type are known, for example from the application EP-A-0,553,424, the patent U.S. Pat. No. 4,648,388, the patent EP-A-0,384,001 and the patent FR-A-92 07 504 (publication No 2,692,471). The anchoring element may be a pedicle screw or hook and the pressure means may be nuts which are screwed on a threaded end of the anchoring element. The connector or connecting clamp may be in two parts or a single part, forming a set of pincers which surrounds the vertebral rod.

When it is in one piece, the surgeon must necessarily insert the rod in the connector in a direction parallel to the longitudinal axis of the rod, which may constitute a troublesome obligation for the surgeon.

These devices are moreover relatively cumbersome in the transverse direction in particular owing to the distance between the anchoring element and the vertebral rod.

An object of the invention is to propose an instrumentation which is less cumbersome and easier for the surgeon to use while giving an excellent mechanical performance over a period of time and therefore good reliability.

According to the invention, each anchoring element has a bearing surface for the rod which is inclined relative to the longitudinal axis of the anchoring element so that the rod may bear against said surface between two points, one of which points, located adjacent to the pressure means, is closer to the anchoring element than the second point; moreover, there is provided in the connector a cavity for the rod which opens at both its ends onto the exterior of the connector and provides at least one bearing point for the rod which is trapped, by the clamping of the pressure means, between said inclined bearing surface and a wall of the cavity, and the latter is extended through a lateral aperture of the connector permitting the insertion of the vertebral rod radially in its cavity.

Owing to this arrangement of the connector, the rod is directly locked on the inclined bearing surface provided on the anchoring element when the pressure means, for example a nut, are clamped onto the connector, which firmly applies the rod against the bearing surface of the anchoring element. Consequently, the overall size of the device in the direction transverse to the rod is considerably reduced relative to known prior instrumentations.

Further, the lateral aperture for inserting the rod in the connector up to its cavity facilitates the work of the surgeon since this lateral insertion is distinctly easier than an insertion in the longitudinal direction of the cavity.

According to other features of the invention:

The inclined bearing surface is flared, for example conical, or is formed by a flat surface.

The anchoring element is made in two parts, one of which carries the bearing surface for the rod and is detachably mounted on the other part. Thus it may concern a ring having a conical outer surface slidably mounted around the anchoring element and capable of abutting against the transverse annular shoulder of said anchoring element.

In an advantageous embodiment of the instrumentation, the cavity of the connector is extended on the side remote from the rod-inserting opening, by a central lateral recess defining two claws on opposite sides of said recess, the edges of the walls of these claws and the bearing surface of the anchoring element providing three points of contact for the rod after clamping of the pressure means and deformation of the rod by the action of these pressure means.

These three points of contact constitute a particularly solid support for the rod after clamping of the compression element on the connector.

Further features and advantages of the invention will appear from the following description, with reference to the accompanying drawings which show several embodiments by way of non-limiting examples.

FIG. 4 is a cross-sectional view partly in elevation of the instrumentation of FIGS. 1 and 2 without the element for compressing the connector on the rod.

FIG. 5 is a view substantially to the scale of the instrumentation of FIGS. 1 to 4 anchored on a vertebra.

FIG. 6 is a view similar to FIG. 2 of a second embodiment of the invention.

Figure 1:
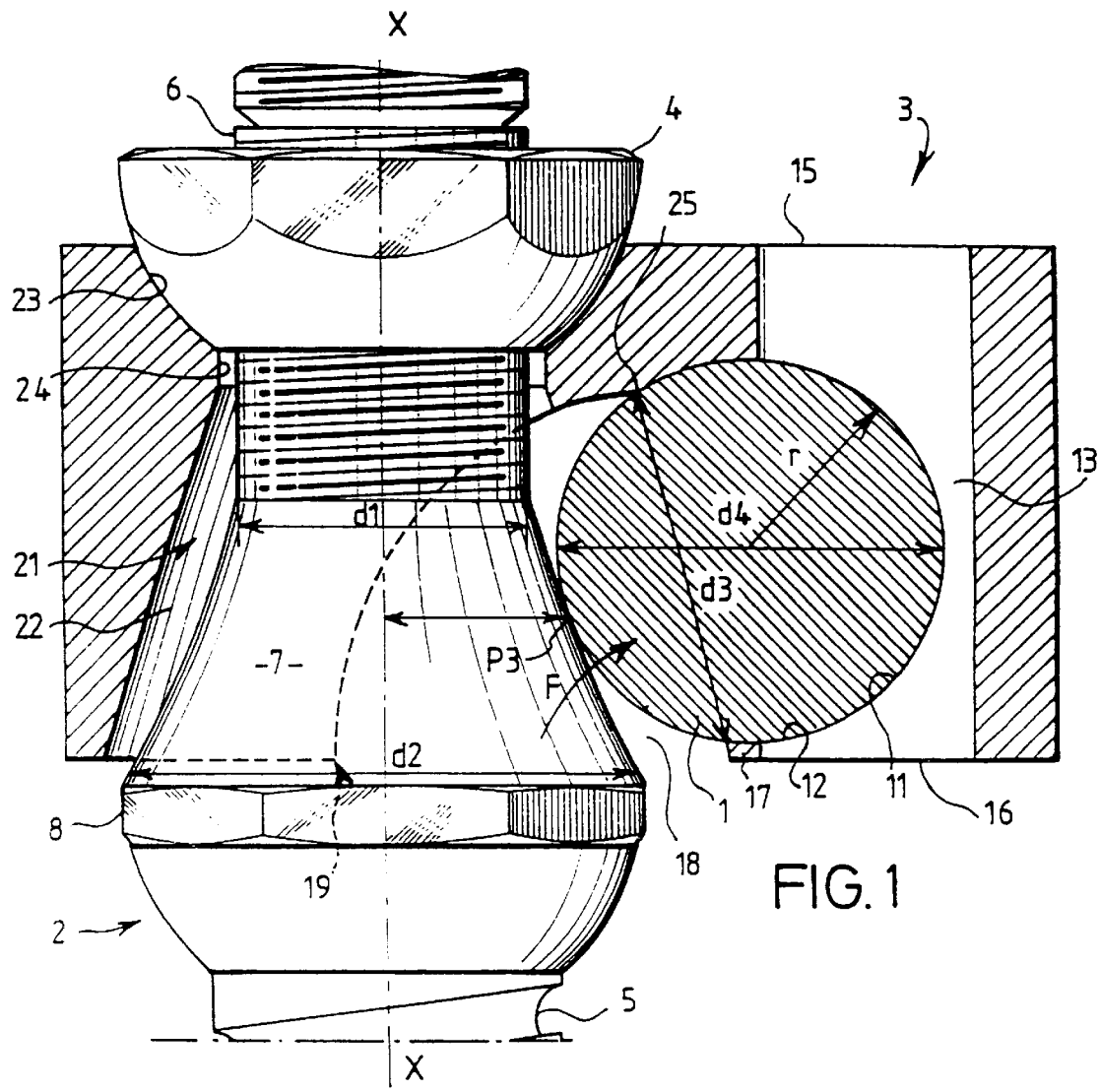
FIG. 1 is a half cross-sectional view and half elevational view, to a larger scale, of a first embodiment of the spinal osteosynthesis instrumentation according to the invention.

The device shown in FIGS. 1 to 4 partly illustrates a spinal osteosynthesis instrumentation intended to prop up the spine for correcting tridimensional deformations of the latter, such as scoliosis.

This instrumentation comprises at least one longitudinal vertebral rod 1, and preferably two rods, extending along a vertebral segment of two or more vertebrae, and vertebral anchoring elements 2 having a longitudinal axis XX and spaced apart along each rod 1. The instrumentation further comprises clamps or connectors 3 providing a connection between the rod 1 and each anchoring element 2, and finally pressure means constituted, in the example of FIG. 1, by a nut 4 having a spherical seat for clamping together the rod 1, the anchoring element 2 and the connector 3.

The anchoring element 2 may be a pedicle screw as partly shown, or a pedicle hook, known per se, adapted to be screwed or anchored on a vertebra V (FIG. 5). The screw 2 is of the type having a double thread and therefore comprises a threaded shank 5 for anchoring in the bone and a threaded portion 6 connected to the threaded shank 5 by a surface 7 of revolution about the axis XX and by a shaped portion 8 for screwing the shank 5 in a pedicle.

A cavity 11 intended for the rod 1 passes right through the connector 3 in a direction perpendicular to the axis XX when the anchoring element 2 is placed in position in the connector 3. The cavity 11 is defined by two cylindrical walls 12 having the same radius of curvature as the radius r of the cylindrical rod 1 and arranged on each side of a central lateral recess passage 13, which is for example cylindrical and arranged on the side remote from that provided for the anchoring element 2. The recess passage 13 laterally extends the cavity 11 and may, as shown, pass right through the connector 3 and open onto the exterior through openings 14, 15. This passage 13 extends in a direction perpendicular to that of the cavity 11 and thereby defines, by its aperture 15, two claws 16 for gripping the rod 1 which they partly surround. The claws 16 may be joined at their ends by a central connecting portion 17 (FIG. 3), or in an alternative arrangement, this connection 17 may be completely eliminated.

Finally, the cavity 11 is extended, on the side remote from the recess passage 13, by a lateral opening 18 defined by the ends of the claws 16 and by an opposite inner edge 19 of the connector 3. This lateral aperture has a width which is sufficient to permit the insertion of the vertebral rod 1 transversely or radially in its longitudinal direction up to its cavity 11 (symbolically represented by the arrow F in FIG. 1).

Also provided in the connector 3 is a through opening 21 which extends coaxially to the longitudinal axis XX of the anchoring element 2 which is itself perpendicular to the rod 1. The opening 21 has a first portion 22 which is flared toward the threaded shank 5, dimensioned to be capable of surrounding with play the inclined surface 7, and a second portion 23 defined in the illustrated example by a spherical bearing surface connected to the first portion 22 by a short cylindrical portion 24. The spherical portion 23 constitutes a bearing surface for the corresponding spherical surface of the nut 4 when the latter is screwed on the threaded portion 6, the anchoring element 2 having been previously inserted in the connector 3 so that its threaded portion 6 extends through the second portion 23 of the opening 21. The flared opening 22 is extended therefore by the cylindrical opening 24 whose diameter exceeds that of the threaded portion 6 so as to allow a large angular movement of the anchoring element 2 with respect to the connector 3, as will be explained in detail hereinafter.

The surface 7 is inclined to its axis of revolution XX so that its smallest diameter d1 is at the base of the threaded portion 6 and its largest diameter d2 is positioned at the level of the abutment 8, the diameter of this surface 7, which is of revolution and flared in the example shown in FIG. 1, therefore increasing from the threaded portion 6 to the abutment 8.

The distance d3 between the opposite edges of the aperture 18 for inserting the rod 1 is defined by an edge 25 on the inner wall of the aperture 18 close to the nut 4 and by the edge 17 of the free ends of the claws 16 and is substantially less than the diameter d4 of the rod 1. This arrangement creates a "hard point" which must be passed through by the rod 1 by exerting a slight force on the latter after having laterally inserted it in the aperture 18. This permits inserting the rod 1 in its cavity 11, the ends of the claws 16 slightly spreading apart in the manner of resilient pincers. These ends of the claws 16 thereafter close onto the rod 1 which is in this way maintained in position by a clipping effect in its cavity so that this rod cannot escape from the connector 3 after the insertion of the anchoring element 2 in the latter.

Further, the cavity 11, the width of its lateral aperture 18 and the rod 1 are so dimensioned that, before the clamping of the connector 3 to the rod and to the anchoring element 2 (situation shown in FIG. 4), the maximum gap d5 between the anchoring element 2 and the edge 17 of the aperture 18 forming the ends of the claws 16 always remains less than the diameter d4 of the rod 1.

This arrangement has the advantage of opposing any escape of the rod 1 out of the connector 3, even after unclipping beyond the edge 25, as soon as the threaded portion 6 of the anchoring element 2 passes through the connector 3, whatever be its angular position in the latter. This angular range of movement of the anchoring element 2 may reach about 30°.

The instrumentation just described is assembled in the following manner:

The surgeon places the anchoring element 2 (FIG. 5) in position in the vertebra V; then he inserts in the connector 3 the portion of the vertebral rod 1 through the lateral aperture 18 up to the cavity 11 in which it is retained by the pinching effect produced by the hard point 25 and the relative flexibility of the claws 16. Then the surgeon slides the connector 3 on the anchoring element 2 through its openings 22, 24, 23 until the rod 1 comes to bear against the inclined surface 7.

Lastly the surgeon screws the nut 4 on the threaded portion 6 until this nut comes in contact with the spherical seat 23 and clamps the assembly in such a manner that the clamping effect of the nut 4 firmly maintains the rod 1 applied against the inclined surface 7.

Figure 2:
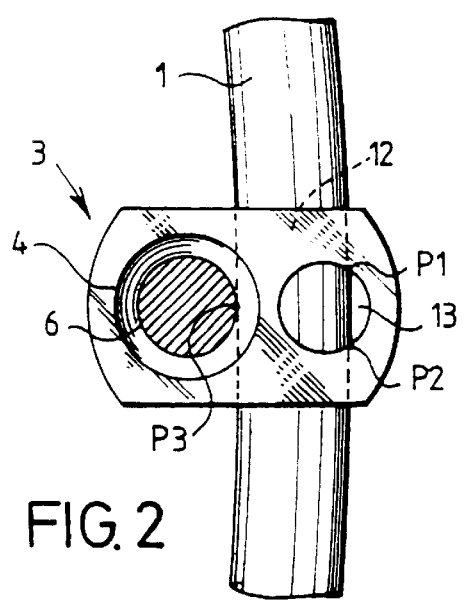
FIG. 2 is a plan view, to a smaller scale, with parts cut away of the instrumentation of FIG. 1.
Figure 3:
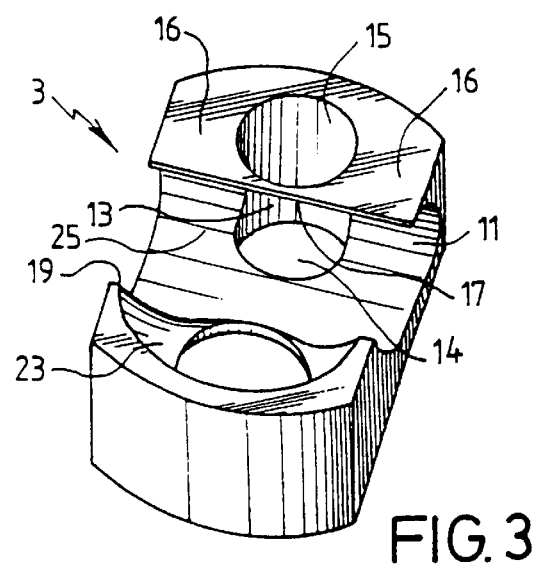
FIG. 3 is a perspective view, to a larger scale, of the connector of the instrumentation of FIGS. 1 and 2.

The device is then in the state shown in FIGS. 1 and 2. Upon the compression of the rod 1 and the connector 3 by the nut 4, the rod 1 undergoes a slight deformation, seen in FIG. 2, which has as a consequence that its surface bears by two points P1, P2 on the edges of the junction between the cavity 11 and the recess passage 13. With the bearing point P3 bearing on the conical surface 7, the rod is therefore clamped in position by three bearing points P1, P2, P3.

It should be noted that it is the arrangement of the central lateral recess passage 13 which permits the creation of the two bearing points P1, P2, the three aforementioned bearing points guaranteeing an excellent clamping of the rod 1 in the chosen position, including the case where the latter is bent.

In the second embodiment shown in FIG. 6, the lateral recess passage 13 is eliminated and only the cylindrical cavity 11 remains. Consequently, at the end of the compression of the connector 3 and the rod 1 against the bearing surface 7, the slightly deformed surface of the rod 1 only bears at a single point P4 on the uninterrupted cylindrical wall of the cavity 11. The two points of contact P3, P4 of the rod 1 still afford a sufficient clamping of the latter, but slightly less effective than that obtained by the three points P1, P2, P3.

Figure 7:
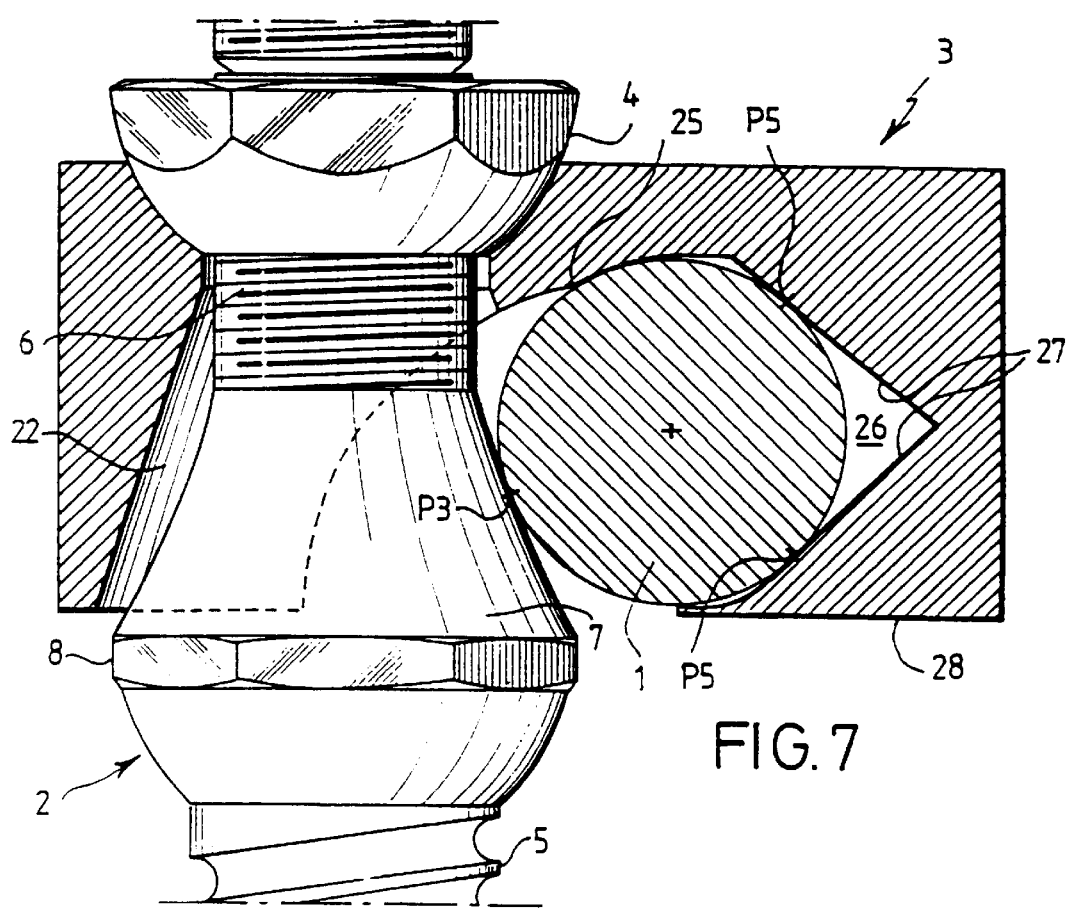
FIGS. 7, 8 and 9 are views similar to FIG. 1 of a third, a fourth and a fifth embodiment of the invention.

The third embodiment of the instrumentation shown in FIG. 7 differs from the embodiment of FIG. 1 by the fact that the cylindrical cavity 11 is here replaced by a cavity 26 having a V-shaped cross section. Consequently the rod 1 bears against each wall 27 of the cavity 26 at two points P5 which provide with the point of contact P3 on the surface 7, an effective clamping of the rod 1 in the chosen position after tightening the nut 4. The lower wall 27 of the cavity 26 terminates in a point affording with the edge 25 the clipping effect on the rod 1.

Figure 8:
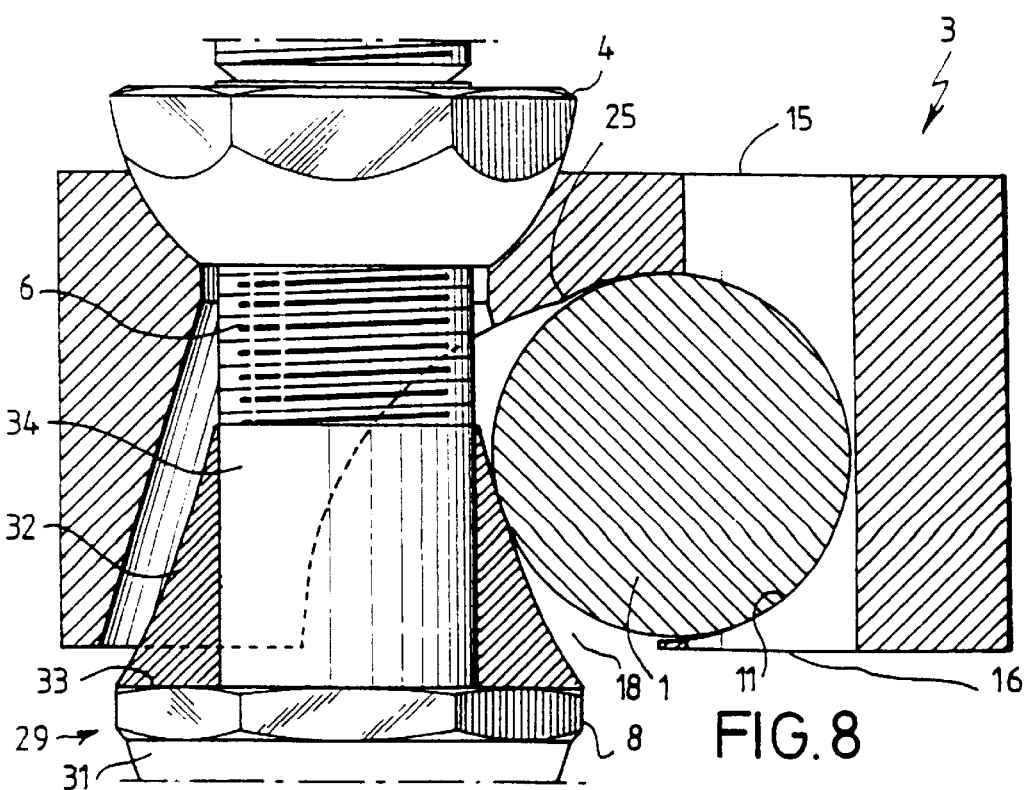

The fourth embodiment of the instrumentation (FIG. 8) differs from the foregoing in that the anchoring element 29 is made in two parts 31, 32, one part 32 carrying the bearing surface for the rod 1 and being detachably mounted on the other part 31. More precisely, the part 32 is a ring having a flared outer surface which is slidably mounted around the threaded portion 6 of the anchoring element 29 and is capable of abutting against a transverse annular shoulder 33. The latter is formed at the junction between a smooth portion 34 extending the threaded portion 6 and the screwing shaped portion 8. The surface of the shoulder 33 is provided with antirotation means for the ring 32, for example serrations (not shown).

Moreover, the manner of assembling and the technical results obtained by the instrumentation of FIG. 7 are similar to the preceding embodiments.

Figure 9:
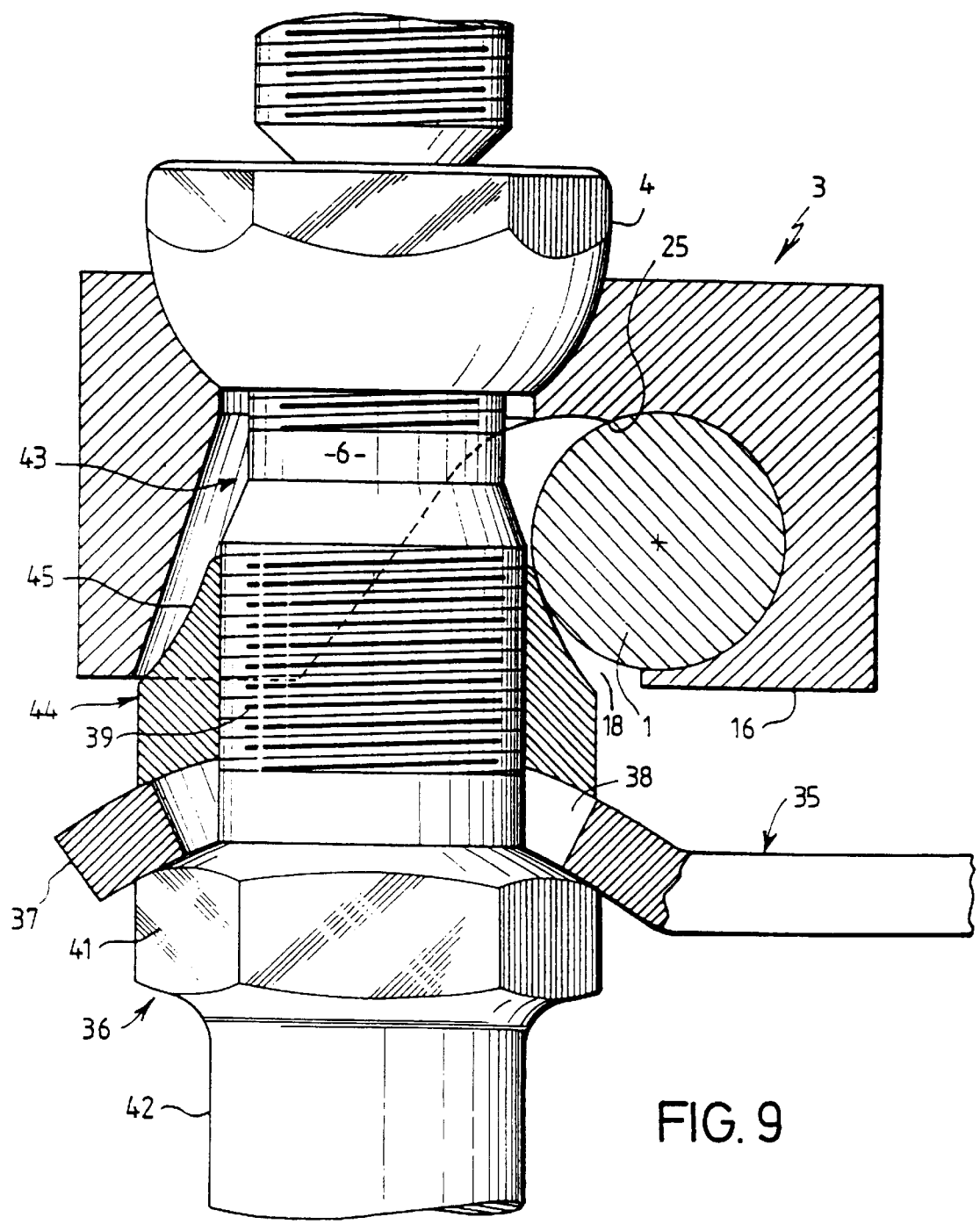

In the fifth embodiment of the invention shown in FIG. 9, the device comprises an additional transverse connecting member 35 for connection with another element (not shown) of the instrumentation which may be a similar assembly of a connector 3, a rod 1 and an anchoring element 36. The end 37 of the connecting member 35 forms a slightly bent tab which is provided with an opening 38 for the passage of a threaded portion 39 of the anchoring element 36 and is capable of bearing against the shaped portion 41 for screwing the anchoring element 36 in the bone.

The threaded portion 39 is connected to a smooth area 43 itself extended by the threaded portion 36 for the screwing of the pressure nut 4. On the threaded portion 39 there may be screwed a nut-ring 44 having an inclined outer surface 45 for bearing against and clamping the rod 1 in the connector 3, this surface 45 being flared in the illustrated example. Consequently, the end 37 of the connection member 35 is interposed between the nut-ring 44 and the abutment 41.

In addition to the previously mentioned technical advantages, the instrumentation according to the invention has that of being particularly compact, owing to the direct bearing of the rod 1 against the anchoring element 2, and therefore a reduced overall size relative to known prior instrumentations. Its utilization by the surgeon is rendered easier by the lateral insertion aperture 18 for the rod 1 and its clipping in the connector 3, which provides increased safety of handling of the elements of the instrumentation.

Various alternative embodiments of the invention may be envisaged. Thus the inclined bearing surface (7, 45 . . . ) for the rod 1 may be formed in various ways, it being formed for example by a flat surface arranged on a projecting portion of the anchoring element 2 or having a conical shape or defined by a mathematical equation.

Likewise, the angular movement of the anchoring element 2 in the connector 3 shown in FIG. 4 has an amplitude which may vary in accordance with the difference between the diameters of the flared opening 22 and the cylindrical opening 24, and the corresponding dimensions of the inclined surface 7 and of the threaded portion 6. The pressure element 4 may have a bearing surface in the connector 3 which is other than spherical, for example conical. Lastly, the threaded portion 6 and the inclined surface 7 may be added to the remainder of the anchoring element 2, for example by a threaded end portion which is screwed inside the abutment 8 and in the adjacent portion of the threaded shank 5.

What is claimed is:

1. Spinal osteosynthesis instrumentation, comprising at least one vertebral rod, at least one vertebral anchoring element having a longitudinal axis, a connector connecting the rod to said anchoring element, said anchoring element including a threaded portion cooperating with pressure means for clamping together said rod, said anchoring element and said connector, wherein said anchoring element has a bearing surface inclined relative to the longitudinal axis of said anchoring element so that said rod can bear against said surface between two points, one of which points is located adjacent to the pressure means and is closer to the axis of said anchoring element than a second of said points, and wherein said connector includes a cavity bounded at least partially by a wall which opens onto the exterior of the connector and provides at least one bearing point for said rod, which is maintained trapped by the clamping of said pressure means between said inclined bearing surface and said wall of said cavity, and wherein said connector defines a lateral aperture opening into said cavity and permitting insertion of said rod radially in said cavity.

2. Instrumentation according to claim 1, wherein said inclined bearing surface is flared.

3. Instrumentation according to claim 2, wherein said anchoring element is made in two parts, one part of which carries said bearing surface and is detachably mounted on the other part.

4. Instrumentation according to claim 3, wherein said anchoring element has a transverse annular shoulder, and said part of said anchoring element carrying said bearing surface is a ring which has a flared outer surface, is slidably mounted around said anchoring element and is capable of abutting against said transverse annular shoulder.

5. Instrumentation according to claim 3, wherein said part of said anchoring element carrying said bearing surface is a nut-ring, and said anchoring element includes a thread cooperating with said nut-ring.

6. Instrumentation according to claim 5, wherein said anchoring element includes a shaped portion for screwing the anchoring element, and further comprising an additional transverse member, one end portion of said member being passed through by said anchoring element and interposed between said nut-ring and said shaped portion.

7. Instrumentation according to claim 1, wherein said cavity of said connector is extended, on the side remote from said aperture for insertion of said rod, by a central recess passage defining two lateral claws on opposite sides of said passage, said claws having walls with edges said edges and said bearing surface of said anchoring element providing three points of contact for said rod after the clamping of said pressure means.

8. Instrumentation according to claim 7, wherein said claws partly surround said rod and said claws have ends that form an edge of said aperture for insertion of said rod in said cavity.

9. Instrumentation according to claim 1, wherein said wall of said cavity of said connector opposed to said anchoring element has a V-shaped section so as to provide said rod with two bearing points in cross section.

10. Instrumentation according to claim 1, wherein said connector includes a flared opening facing said bearing surface of said rod for the passage of said anchoring element, said opening being extended by an aperture whose diameter is greater than that of a threaded portion of said anchoring element so as to allow a large range of angular movement of said anchoring element relative to said connector.

11. Instrumentation according to claim 1, wherein said cavity, the width of said lateral aperture, and said rod, are so dimensioned that before the clamping of said connector on said rod and on said anchoring element, the maximum gap between said anchoring element and said aperture for insertion of said rod is smaller than the diameter of said rod.

12. Instrumentation according to claim 1, wherein said pressure means includes a bearing surface which is adapted to a complementary surface of said connector.

13. Instrumentation according to claim 12, wherein said pressure means is formed by a screw capable of axially screwing onto said anchoring element.

14. Instrumentation according to claim 2, wherein said inclined bearing surface is conical.

15. Instrumentation according to claim 1, wherein said inclined bearing surface is formed by a flat surface.

16. Instrumentation according to claim 4, wherein said transverse annular shoulder is provided with antirotation means.

17. Instrumentation according to claim 8, wherein said ends of said claws are connected together by a connection.

18. Instrumentation according to claim 8, wherein said ends of said claws are separated so as to form two distinct claws.

19. Instrumentation according to claim 12, wherein said bearing surface of said pressure means is curved.

20. Instrumentation according to claim 18, wherein said bearing surface of said pressure means is one of spherical or conical.

21. An apparatus, comprising:

an elongated member;

a bone anchoring element having a longitudinal axis and a bearing surface inclined relative to said longitudinal axis adapted to bear against said elongated member;

a connector connecting said elongated member to said anchoring element, said connector having a cavity for accommodating said elongated member bounded at least partially by a wall which opens onto the exterior of the connector and provides at least one bearing point for said elongated, said connector further defining a lateral aperture opening into said cavity and permitting insertion of said rod radially into said cavity; and pressure means cooperating with said anchoring element for clamping together said elongated member, said anchoring element and said connector, whereby said rod is maintained trapped between said inclined bearing surface and said wall of said cavity.

22. The apparatus of claim 21, wherein said inclined bearing surface is on an exterior portion of said anchoring member.

23. The apparatus of claim 22, wherein said inclined bearing surface is substantially conical.

24. The apparatus of claim 22, wherein said inclined bearing surface has a concave portion.

25. The apparatus of claim 22, wherein said anchoring member has a top portion and a bottom portion, said bottom portion including threads adapted to engage a bone.

26. The apparatus of claim 25, wherein said inclined bearing surface extends outward from said longitudinal axis as said inclined bearing surface extends toward said bottom portion of said anchoring member.

27. The apparatus of claim 21, wherein said wall of said connector is a curved surface.

28. The apparatus of claim 21, wherein said wall of said connector includes multiple sections.

29. The apparatus of claim 28, wherein one of said wall sections has a substantially flat portion.

30. The apparatus of claim 29, wherein two of said wall sections each include substantially flat portions that intersect with each other.

31. The apparatus of claim 28, wherein one of said wall sections has a curved portion.

32. The apparatus of claim 21, wherein said wall includes a curved portion and a substantially flat portion.

33. The apparatus of claim 21, wherein said connector includes a hole adapted to accommodate said anchoring element and an upper surface around a portion of said hole, said surface adapted to mate with said pressure means.

34. The apparatus of claim 33, wherein said hole is flared to allow a range of angular movement of the anchoring element relative to the connector.

35. The apparatus of claim 33, wherein said upper surface is substantially concave.

36. The apparatus of claim 21, further comprising a transverse member, said transverse member having a portion with an aperture therethrough, wherein said anchoring member is positioned within said aperture and said transverse member is clamped to said anchoring member and said connector.

37. The apparatus of claim 21, wherein said anchoring element includes a first and second part, said first part carrying said inclined bearing surface and being detachably mounted on said second part.

38. The apparatus of claim 37, wherein said second part of said anchoring element has a transverse annular shoulder, and said first part of said anchoring element abuts said transverse annular shoulder.

39. The apparatus of claim 38, wherein said first part of said anchoring element is substantially a ring which is one of slidably and threadably mounted on said second part of said anchoring element.

40. The apparatus of claim 37, wherein at least one of said first and second parts of said anchoring member includes antirotation means.

41. The apparatus of claim 21, wherein said cavity, said lateral aperture and said elongated member are dimensioned so that the maximum gap between said anchoring element and the edge of said lateral aperture is smaller than the diameter of the elongated member.

42. The apparatus of claim 21, wherein said cavity is extended by a central recess passage defining two lateral claws.

43. The apparatus of claim 41, wherein said claws are connected by a connecting portion.

* * * * *